(12) United States Patent
Cho et al.

(10) Patent No.: US 8,871,957 B2
(45) Date of Patent: Oct. 28, 2014

(54) METAL CATALYST COMPOSITION FOR PRODUCING FURFURAL DERIVATIVES FROM RAW MATERIALS OF LIGNOCELLULOSIC BIOMASS, AND METHOD FOR PRODUCING FURFURAL DERIVATIVES USING THE COMPOSITION

(75) Inventors: Jin Ku Cho, Gyeonggi-do (KR); Sangyong Kim, Chungcheongnam-do (KR); Dohoon Lee, Seoul (KR); Bora Kim, Daejeon (KR); Jaewon Jeong, Seoul (KR)

(73) Assignee: Korea Institute of Industrial Technology, Chungcheongnam-do (KR)

( * ) Notice: Subject to any disclaimer, the term of this patent is extended or adjusted under 35 U.S.C. 154(b) by 49 days.

(21) Appl. No.: 13/640,764

(22) PCT Filed: Apr. 14, 2011

(86) PCT No.: PCT/KR2011/002681
§ 371 (c)(1),
(2), (4) Date: Oct. 12, 2012

(87) PCT Pub. No.: WO2011/129640
PCT Pub. Date: Oct. 20, 2011

(65) Prior Publication Data
US 2013/0030194 A1    Jan. 31, 2013

(30) Foreign Application Priority Data
Apr. 15, 2010 (KR) .................. 10-2010-0034646
Feb. 16, 2011 (KR) .................. 10-2011-0013821

(51) Int. Cl.
*C07D 307/48* (2006.01)
*B01J 27/13* (2006.01)
*B01J 27/132* (2006.01)
*B01J 23/652* (2006.01)
*B01J 31/02* (2006.01)
*C07D 307/50* (2006.01)
*B01J 37/04* (2006.01)
*B01J 23/46* (2006.01)

(52) U.S. Cl.
CPC ............ *B01J 27/132* (2013.01); *B01J 27/13* (2013.01); *B01J 23/6522* (2013.01); *B01J 31/0225* (2013.01); *C07D 307/50* (2013.01); *C07D 307/48* (2013.01); *B01J 37/04* (2013.01); *B01J 23/462* (2013.01); *B01J 31/0284* (2013.01); *B01J 31/0227* (2013.01)
USPC ........................................................ 549/489

(58) Field of Classification Search
CPC ........................... B01J 23/462; C07D 307/48
USPC ........................................................ 549/489
See application file for complete search history.

(56) References Cited

U.S. PATENT DOCUMENTS

| | | | |
|---|---|---|---|
| 7,939,681 B2 | 5/2011 | Zhao et al. | |
| 2010/0004437 A1 | 1/2010 | Binder et al. | |
| 2010/0317879 A1 | 12/2010 | Zhao et al. | |

FOREIGN PATENT DOCUMENTS

| | | |
|---|---|---|
| KR | 20000031378 | 1/2002 |
| KR | 20040044933 | 5/2004 |
| KR | 20090024664 | 3/2009 |
| WO | 2007/104515 A1 * | 9/2007 |
| WO | 2009/030512 A2 * | 3/2009 |
| WO | WO2009030551 A1 | 3/2009 |
| WO | 2009/076627 A2 * | 6/2009 |

OTHER PUBLICATIONS

Donohoe et al., Org. Let. (2007), vol. 9(6), pp. 953-956.*
Article—Su et al., "Single-step conversion of cellulose to 5-hydroxymethylfurfural (HMF), a versatile platform chemical," *Applied Catalysis A: General*, vol. 361, 2009, pp. 117-122.
Search Report for PCT/KR2011/002681 dated Dec. 9, 2011, 2 pages.

* cited by examiner

*Primary Examiner* — Taofiq A Solola
(74) *Attorney, Agent, or Firm* — Dority & Manning, P.A.

(57) ABSTRACT

The present invention relates to a metal catalyst composition for producing furfural derivatives from raw materials of lignocellulosic biomass, and method for producing furfural derivatives using the composition. The present invention comprises ruthenium chloride ($RuCl_3$) and chromium chloride ($CrCl_2$). The chromium chloride ($CCl_2$) is from 300 to 500 parts by weight on the basis of 100 parts by weight of the ruthenium chloride ($RuCl_3$). Unlike conventional furfural derivatives producing process that should go through multi step processes such as pre-process, saccharification process, etc., the present invention has an advantage of producing furfural derivatives from lignocellulosic raw material only through simple reaction process in one reaction apparatus by mixing various kinds of metal catalyst at an optimum ratio.

13 Claims, 3 Drawing Sheets

METAL CATALYST COMPOSITION FOR PRODUCING FURFURAL DERIVATIVES FROM RAW MATERIALS OF LIGNOCELLULOSIC BIOMASS, AND METHOD FOR PRODUCING FURFURAL DERIVATIVES USING THE COMPOSITION

CROSS REFERENCE TO RELATED APPLICATION

This application is the national stage entry of International Patent Application No. PCT/KR2011/129640 having a filing date of Apr. 14, 2011, which claims priority to and the benefit of Korean Patent Application No. 10-2010-0034646 filed in the Korean Intellectual Property Office on Apr. 15, 2010 and Korean Patent Application No. 10-2011-0013821 filed in the Korean Intellectual Property Office on Feb. 16, 2011, the entire contents of which are incorporated herein by reference.

BACKGROUND OF THE INVENTION

1. Field of the Invention

The present invention relates to a metal catalyst composition for producing furfural derivatives from raw materials of lignocellulosic biomass, and method for producing furfural derivatives using the composition. More particularly to the composition and the method which may turn lignocellulosic biomass raw materials to furfural derivatives through single step process without additional saccharification process by using various kinds of metal catalyst in optimal reacting condition, thus significantly reducing process costs, unlike conventional composition and method going through multi step process.

2. Description of the Related Art

Continuous reduction in limited oil resources and dramatic increase in oil demand due to the rapid growth of emerging countries like the BRICs cause the imbalance between demand and supply of oil, which leads to the era of high oil prices. Large amount of green house gases are emitted irreversibly due to reckless use of non-cyclic oil resources, and thus cause a serious environment problem like global warming. Because of those circumstances, most of countries come up with tough regulation of imposing costs on the amount of emitted green house gases to pose tough sanctions on the use of the non-cyclic oil resources.

Advanced countries are already taking great efforts to replace the oil resources with renewable and sustainable resources like biomass. For those efforts they are industrially producing biofuels such as bioethanol, biodiesel, and biomass-derived chemical materials such as lactic acid and propanediol which are raw materials for polymer elements.

However, the industrially produced biomass derived fuels and raw materials in current times use crop biomass resources such as glucide group (sugar cane, sugar beet, etc) and starchy group (corn, potato, sweet potato, etc) which are used for food as supply sources. This leads to a drop in agricultural lands, a rise in grain prices and current controversy about global food problem in the international community.

In order to solve those problems, attentions are drawn to plants that grow naturally with great vitality on non-cultivated lands, crop residue after cultivation and carbohydrates such as celluloses and hemicelluloses that can be extracted from lignocellulosic biomasses such as waste lignocellulosic resources, etc. The cellulose and hemicelluloses are regarded as replaceable by carbohydrates sucroses or starches coming from starchy group.

The extractable carbohydrate polymers celluloses and hemicelluloses from lignocellulosic biomass are produced in large amounts (production volume: 127 billion ton per year) every year through photosynthesis, and only 3-4% of the production volume is currently used. Due to the reason, advanced countries such as the U.S., Europe, Japan, etc are actively carrying out research on utilizing celluloses and hemicelluloses produced from lignocellulosic biomass. The carbohydrate polymers produced from lignocellulosic biomass are polysaccharides whose hexose or pentose structure is connected 1 or 2-dimmentionally. Normally the polysaccharides turn to hexose glucoseor or hexose fructose, and pentose xylose through hydrolysis saccharification process, and then they are applied to the next organism fermentation or catalyst chemical processes through separation and purification process. Specifically, commonly used production method for obtaining the final target compound from lignocellulosic biomass raw materials comprises; a pre-process (a) for extracting polysaccharides carbohydrate polymers from biomass supply source; a saccharification process (b) for obtaining hexose glucose or hexose fructose and pentose xylose; and a separation and purification process (c) of produced monosaccharide compound; and a organism fermentation or catalyst chemical multi-stage process (d) for obtaining final compound. However, the multi-stage processes cause an increase in production costs and a decreased in yield.

The furfural derivatives compound from biomass is currently drawing a lot of attention. The hexose derived 5-hydroxymethyl-2-furfural and pentose derived 2-furfural are typical core platforms and are widely applicable for next generation biofuels, bio-based plastics monomer and adhesives, and eco-friendly adhesives and coating agents fine chemistry products. A research on mass production methods of those products is being actively carried out.

[A Structural Formular of 2-Hydroxy-Methyl Furfural]

[A Structural Formular of 2-Furfural]

The typical technology for producing HMF from derived carbohydrates from biomass has a method for obtaining HMF in acid catalyst condition thorough dehydration reaction with fructose that serves as a starting material. This method has an advantage of easily obtaining furan structure without additional isomerization reaction unlike pentose fructose and hexose sugar compounds. Dumesic's group at the University of Wisconsin-Madison reported on a technology for producing HMF under various solvent conditions through acid catalyst conversion reaction with fructose that serves as a starting material (Science, 2006, 312, 1933-1937). According to the report, the technology showed high process efficiency by obtaining high HMF concentration (30 wt %).

However, for fructose, it has limited supply source as the starting material and exists only in agricultural productions. In the technology above, the solvents with optimum performance has the high boiling point, and thus high-energy distillation process is required to eliminate the boiling point, which requires new separation process technology.

Besides, a saccharification process for effectively obtaining glucose from polysaccharide cellulose is required and this is the problem for the fructose.

Meanwhile, 2-furfural is usable itself as a fuel material. Furfuryl alcohol and furfuryl acid derivatives from oxidation-reduction process are compounds that are used as polymer elements raw materials and are obtained through dehydration reaction under the acid condition of hemicellulose existed in lignocellulosic biomass. However, the performing condition of the dehydration reaction through sulfuric acid and strong acid is poor and cause a huge amount of waste acid and waste water.

So, developing a method for simply manufacturing furfural derivatives without complex and high-cost pre-process and saccharification process is required.

DETAILED DESCRIPTION OF THE EMBODIMENTS

The present invention is intended to solve the problems described above. The conventional invention should go through multi step processes such as pre-process and saccharification process. The present invention could directly turn cellulose or lignocellulosic biomass raw materials to furfural derivatives through simple reaction process in one reaction apparatus by mixing various kinds of metal catalyst at an optimum ratio.

Also, the present invention is aimed to reduce material costs and turn lignocellulosic biomass raw materials to furfural derivatives effectively by applying best optimized process to the lignocellulosic biomass and using the lignocellulosic biomass as raw material that does not cause food problem. The present invention is aimed to significantly reduce process costs and increase the yield as the furfural derivatives may be produced directly through simple process. The present invention is also aimed to be environment-friendly as they avoid waste acid and waste water which are caused through pre-process and saccharification process, etc, and reduce energy loss.

Moreover, the present invention does not have to extract cellulose from lignocellulosic biomass raw materials and utilize the useful component hemicellulose directly in lignocellulosic biomass raw materials.

The products of the present invention are very useful and effective as they may be used widely in various fields through various conversion reactions as typical core platform materials, and are optimized for converting 2-hydroxy-methyl furfural and 2-furfural immediately.

In order to achieve those goals described above, the metal catalysts for producing furfural derivatives directly from lignocellulosic biomass raw materials comprise a ruthenium and a chrome.

The chrome is from 300 to 500 parts by weight on the basis of 100 parts by weight of the ruthenium, further comprises a solvent and the solvent is at least one of an ionic solvent and an aprotic polar solvent.

The ionic solvent is at least one of ethylmethylimidazolium chloride ([EMIM]Cl), ethylmethylimidazolium bromine ([EMIM]Br) or ethylmethylimidazolium iodine ([EMIM]I), the aprotic polar solvent is at least one of dimethylacetamide, dimethyl sulfoxide, dimethylformamide, hexamethylphosphorous triamide, N-methylpyrrolidone, tetrahydrofuran or γ-butylorac.

Next, a method for producing furfural derivatives from lignocellulosic biomass raw materials comprises a pre-processing lignocellulosic biomass to extract cellulose; and a reacting metal catalyst MXn or MXn.H$_2$O through catalyst conversion reaction in solvent to produce 5-hydroxy (the metal element, X is selected from the functional group consisting of halogen element, triflate, nonaflate, mesylate, tosylate or diazonium, and the n is from 1 to 3).

For the metal catalyst, the metal element (M) comprises at least one of Cr (□) metal catalyst and Ru (□) metal catalyst and the equivalence ratio of the metal catalyst comprising the Cr (□) to the metal catalyst comprising the Ru (□) is from 1:1 to 5:1. The ratio of the cellulose to the solvent is from 50 g/L to 500 g/L, and the equivalent of the metal catalyst is from 0.5 mol % to 200 mol %.

When reacting metal catalyst MXn or MXn.H$_2$O through catalyst conversion reaction in solvent to produce 5-hydroxy, the temperature of reacting is from 100° C. to 150□, and the time of reacting is from 1 to 5 hours.

Next, a method for producing furfural derivatives from lignocellulosic biomass raw materials comprises a mixing a metal catalyst and a solvent to produce a compound; a heating the compound; an adding lignocellulosic biomass raw materials to the compound to produce reaction materials; and a reacting the reaction materials to heat and react it.

When mixing a metal catalyst and a solvent to produce a compound, the metal catalyst is comprised of MXn or MXn.H$_2$O, the M is a metal element, the X is selected from the functional group consisting of halogen element, triflate, nonaflate, mesylate, tosylate or diazonium, and the n is from 1 to 3.

Also, when mixing a metal catalyst and a solvent to produce a compound, the metal element is one of Mn, Ni, Fe, Cr, Cu, Co, Ru, Sn, Zn, Al, Ce, La, Nd, Sc, Yb or In.

When mixing a metal catalyst and a solvent to produce a compound, the metal catalyst is consisted of a ruthenium and a chrome, and the chrome is from 300 to 500 parts by weight on the basis of 100 parts by weight of the ruthenium.

Also, when mixing a metal catalyst and a solvent to produce a compound, the solvent is at least one of ionic solvent and aprotic polar solvent, and the ionic solvent is at least one of ethylmethylimidazolium chloride, ethylmethylimidazolium bromine or ethylmethylimidazolium iodine, and the aprotic polar solvent is at least one of dimethylacetamide, dimethyl sulfoxide, dimethylformamide, hexamethylphosphorous triamide, N-methylpyrrolidone, tetrahydrofuran or γ-butylorac.

When heating the compound, the temperature of reacting is from 60° C. to 100° C., and when adding producing reaction materials by adding lignocellulosic biomass to the compound, the lignocellulosic biomass raw material is consisted of at least one of cellulose or hemicellulose. Also, when adding lignocellulosic biomass raw materials to the compound to produce reaction materials, the metal catalyst is from 1 mole % to 20 mole % on the basis of 100 mole % of the lignocellulosic biomass raw material, and when adding lignocellulosic biomass raw materials to the compound to produce reaction materials, the lignocellulosic biomass raw material is from 50 g to 500 g on the basis of 1 L solvent, and when reacting heating and reacting the reaction materials, the temperature of reacting is from 100° C. to 150° C. and the time of reacting is from 1 to 4 hours.

The present invention solves the problem of a rise in crop prices by utilizing celluloses derived from lignocellulosic biomass, and also possibly reduces process costs by catalyst conversion reaction that converts the product itself through single step process without saccharification process for producing monosaccharide from celluloses to glucoses.

Raw materials prices could be reduced by using lignocellulosic biomass raw materials not causing food problem and the lignocellulosic biomass raw materials could be effectively turned to furfural derivatives by applying optimized process to the lignocellulosic biomass.

Also, furfural derivatives could be directly produced from lignocellulosic biomass raw materials through simple process, process costs are significantly reduced, and the yield increases.

Waste acid and waste water are avoided from pre-process and saccharification process and energy consumption is significantly reduced, which are eco-friendly.

Cellulose does not have to be additionally extracted and the useful component, hemicelluloses in lignocellulosic biomass raw materials is directly utilized.

The present invention is optimized to turn lignocellulosic biomass raw materials to 2-hydroxy-methyl furfural and 2-furfural. Those product materials are very useful and effective as they are widely used in various fields through various conversion reactions as typical platform materials.

DETAILED DESCRIPTION OF THE EMBODIMENTS

A metal catalyst composition for producing furfural derivatives from raw materials of lignocellulosic biomass, and method for producing furfural derivatives using the composition are described here in detail in reference to attached drawings. The present invention could be well appreciated through preferable examples aimed at illustrating present invention's purpose. However, this is not intended to narrow the protection rights scope which is limited by attached claims.

The first example of the composition of the present invention comprises $MX_n$ or $MX_n.H_2O$, the M is a metal element, the X is selected from the functional group consisting of halogen element, triflate, nonaflate, mesylate, tosylate or diazonium, and the n is from 1 to 3.

It is desirable that the functional group comprises halogen elements such as Cl, Br, I, etc. The corresponding functional group is one at least of triflate, nonaflate, methylate, ethylsulfonate, benzensulfonate, tosylate, tri-isopropyl benzensulfonate, formate, acetate, trifluoroacetate, nitrobenzoate, and halogen arylcarboxylate. In particular, it is also desirable to use boron benzonate, methyl carbonate, ethyl carbonate, benzyl carbonate, t-butyl carbonate, dimethyl phosphonate, diethyl phosphonate, diphenyl phosphonate or diazonium. More preferably, it is most effective to use one of functional groups consisting of halogen element, triflate, nonaflate, mesylate, tosylate or diazonium.

It is effective to use one metal element of Mn, Ni, Fe, Cr, Cu, Co, Ru, Sn, Zn, Al, Ce, La, Nd, Sc, Yb or In for improving conversion efficiency.

Through various experiments, the metal catalyst composition of the present invention is proved to be most effective for the reaction of converting lignocellulosic raw material to furfural derivatives directly.

It is desirable that the $MX_n$ or $MX_n.H_2O$ is from 1 mole % to 20 mole % on the basis of the 100 mole % lignocellulosic biomass raw material. More preferably, from 5 mole % to 10 mole % for the $MX_n$ or $MX_n.H_2O$ is effective. When the mole % of the $MX_n$ or $MX_n.H_2O$ is below 1 mole %, the conversion is almost impossible because catalyst is difficult to perform. Even though the conversion is possible, there is a problem of the low conversion rate. When the mole % of the $MX_n$ or $MX_n.H_2O$ is above 20 mole %, the economic value and the yield drops.

Next, the second example for producing furfural derivatives from lignocellulosic biomass raw materials comprises a ruthenium and a chrome. More preferably, it is effective for the second example to comprise $RuCl_3$ and $CrCl_2$. The $RuCl_3$ and $CrCl_2$ are the most effective metal catalyst and perform their unique role most effectively in hydrolysis, dehydration and isomerization reactions as they are comprised of various kinds of metal catalysts.

Here, the ruthenium and the chrome perform various kinds of reaction at the same time by mixing them because the ruthenium serves as a lewis acid for hydrolysis and dehydration reactions, and the chrome is effective for isomerization reaction.

Also, it is desirable that the chrome is from 300 to 500 parts by weight on the basis of 100 parts by weight of the ruthenium. More preferably, the chrome's parts by weight from 350 to 450 is effective. When the chrome's parts by weight is below 300 or above 500, it is out of the most effective compound rate range and this leads to significant decrease in the final product's yield.

Next, it is desirable to further comprise solvent in the first and the second examples. The solvent is effective to be at least one of ionic solvent and aprotic polar solvent. This helps the conversion reaction.

The ionic solvent is desirable to be at least one of ethylmethylimidazolium chloride, ethylmethylimidazolium bromine or ethylmethylimidazolium iodine, and the aprotic polar solvent is effective to be at least one of dimethylacetamide, dimethyl sulfoxide, dimethylformamide, hexamethylphosphorous triamide N-methylpyrrolidone, tetrahydrofuran or γ-butylorac.

It is possible to convert lignocellulosic biomass material to furfural derivatives directly because the metal catalyst composition for producing furfural derivatives from lignocellulosic biomass materials of the present invention is optimized in the second example of producing method of furfural derivatives. So, the metal catalyst composition for producing furfural derivatives from lignocellulosic biomass materials of the present invention is in common with the technical features of the metal catalyst used in the first example of furfural derivatives producing method, but the compound rate may be different.

Figure 1:
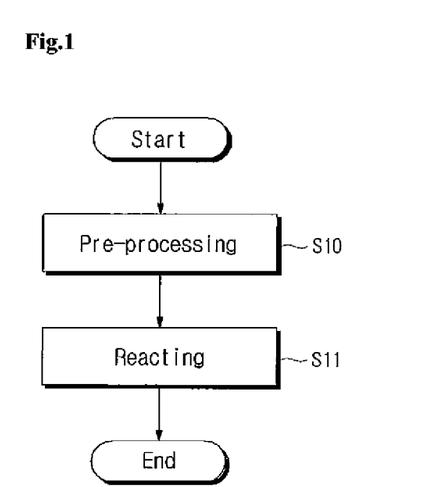
FIG. 1 is a flowchart of a method for producing furfural derivatives according to the first example of the present invention.

Next, the first example of producing furfural derivatives of the present invention comprises a pre-processing (S10) lignocellulosic biomass to extract cellulose and a reacting (S11)

cellulose and metal catalyst in solvent through catalyst conversion reaction to produce furfural derivatives. Now, each process will be looked over.

The pre-processing (S10) is pre-processing lignocellulosic biomass to extract cellulose that is used as starting material in the reacting (S11).

The lignocellulosic biomass grows naturally in nature and it is a wood waste in city or a wood by-product in forests. Preferably, the lignocellulosic biomass could be a plant that grows naturally with great vitality on non-cultivated lands (switchgrass, etc), crop residue after cultivation (rice straw, corn stalk, etc) and waste wood resources (waste wood, waste paper, etc).

Any method could be used limitlessly for extracting cellulose from lignocellulosic biomass resources. In terms of chemical composition, the amount of cellulose through pre-processing from lignocellulosic biomass resources varies according to plants, but it is known that the amount exists about 33% in average, 50% in trees and 90% in cottons. The important main rest components are pentose natural polymer hemicellulose and aromatic phenols lignin. Normally, during the pre-processing (S10), the lignin is separated and removed by dissolving the lignin in the alkaline condition, and hemicellulose that is weaker acid than cellulose could be separated by dealing with weak acid.

The extracted cellulose through this way is a natural polymer comprising D-glucose as monomer. The extracted cellulose forms glycosidic bond in the C1 and C4 position of glucose and is linked through β(1→4) bond as shown in chemical formula 1 below.

[Chemical Formula 1]

The reacting (S11) is producing furfural derivatives through catalyst conversion reaction of the cellulose and the metal catalyst in solvent. According to the reacting for the first example of the present invention, furfural derivative could be obtained through single step reaction without the processing of converting the starting material cellulose to monomer through hydrolysis. In the reaction formula 1 below, the processing of obtaining 5-hydroxymethyl-2-furfural through single step reaction using cellulose is simply shown as preferable one example.

[Reaction Formula 1]

-continued

As described by inventors of the present invention, various kinds of metal catalysts were used to materialize hydrolysis reaction (saccharification reaction) (a), isomerization reaction (b) and dehydration reaction (c) at the same time in one reaction apparatus. For this, they tried finding the optimum metal catalyst conversion reaction condition by changing various reaction conditions such as kinds of metal catalyst, combination of various kinds of metal catalyst, composition rate, temperature, time and solvent of the various kinds of metal catalyst when mixing them.

Metal catalyst used in the reacting (S11) of the present invention serves as a lewis acid to accelerate hydrolysis and dehydration reactions, and the metal catalyst mediated the isomerization reaction that converts hexose cellulose to pentose cellulose.

Here, if metal catalyst used in one example of the present invention are MXn or MXn.H$_2$O materials could be used not being specially limited. The M is a metal element, the X comprises halogen element, the X is corresponding functional group, and n is from 1 to 3.

For example, the metal catalyst comprises Cl, Br, I, etc and halogen element, and the corresponding functional group is one of triflate, nonaflate, methylate, ethylsulfonate, benzensulfonate, tosylate, tri-isopropyl benzensulfonate, formate, acetate, trifluoroacetate, nitrobenzoate, and halogen arylcarboxylate. In particular, the corresponding functional group is one of boron benzonate, methyl carbonate, ethyl carbonate, benzyl carbonate, t-butyl carbonate, dimethyl phosphonate, diethyl phosphonate, diphenyl phosphonate or diazonium. Among these, preferably, it is desirable to apply one of functional group of halogen element, triflate, nonaflate, methylate, tosylate or diazonium.

Here, the preferable applicable metal element is selected from a group consisting of Mn, Ni, Fe, Cr, Cu, Co, Ru, Zn, Al, Ce, La, Nd, Sc, Yb and In. As described later, in particular, the metal catalyst comprising Cr (II) as a metal element, for example, CrCl$_2$, CrCl$_2$.H$_2$O, CrBr$_2$, chrome triplate, chrome acetate or/and the metal catalyst comprising Ru (III) as a metal element, for example, RuCl$_3$, RuCl$_3$.H$_2$O, RuBr$_3$, ruthenium tosylate, etc, showed preferable yield.

The solvent used for the reacting (S11) of the present invention is desirable to be an ionic solvent such as ethylmethylimidazolium chloride, ethylmethylimidazolium bromine or ethylmethylimidazolium iodine, etc, and an aprotic polar solvent such as dimethyl acetamide (DMA), dimethyl sulfoxide (DMSO), dimethyl formamide (DMF), hexamethyl phosphorous triamide, N-methylpyrrolidone, tetrahydrofuran or γ-butylorac. In particular, an ionic solvent is preferably used as a solvent.

Also, the preferable ratio of the added cellulose to the solvent is from 50 g/L to 500 g/L. More preferably, the ratio of the added cellulose to the solvent is from 100 g/L to 300 g/L (wt/V), and high yield was shown when applying the ratio of the added cellulose to the solvent (from 100 g/L to 300 g/L). Moreover, the whole equivalent of the metal catalyst to maximize yield is from 0.5 mole % to 20 mole %, and more preferably the whole equivalent of the metal catalyst is from 5 mole % to 10 mole %. It is desirable to use more than two kinds of metal catalysts at the same time and the each used metal catalyst is selected to serve its unique role in hydrolysis, isomerization and dehydration reactions.

As proven in many experiments, the best condition happens when Ru(III) is preferably used as a metal catalyst that serves a lewis acid for hydrolysis and dehydration reactions and Cr(II) is used as metal catalyst for isomerization reaction.

Achieving optimum composition rate of various kinds of metal catalyst is important because composition rate of various kinds of metal catalyst affects a yield of final products. When using the metal catalyst combination, the preferable composition rate of Cr (II) metal catalyst and Ru (III) metal catalyst (Cr (II): Ru (I), equivalent rate, mole rate) is from 1:1 to 5:1, and in particular 4:1 is preferable.

The preferable reaction temperature is above 100° C. according to one example, the temperature of from 100° C. to 150° C. is more preferable, and the reaction time is from 1 hour to 5 hours.

Figure 2:
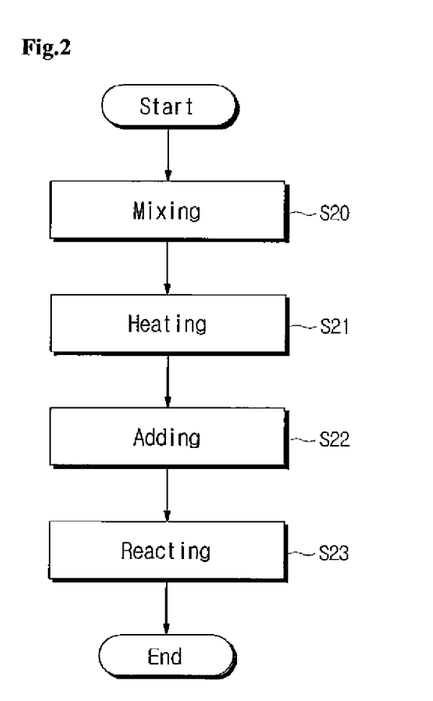
FIG. 2 is a flowchart of a method for producing furfural derivatives according to the second example of the present invention.

Next, the second example of producing method for furfural derivatives comprises mixing (S20), heating (S21), adding (S22) and reacting (S23) as shown in FIG. 2.

Here, the mixing (S20) is mixing metal catalyst and solvent to produce compound, which is a process of mixing metal catalyst and solvent effectively to facilitate them in the reaction. When mixing metal catalyst and solvent to produce compound (S20), the metal catalyst is MXn or MXn.$H_2O$, the M is a metal element, the X is one of functional group consisting of halogen element, triflate, nonaflate, mesylate, tosylate or diazonium, and the n is from 1 to 3. The metal element is one of Mn, Ni, Fe, Cr, Cu, Co, Ru, Sn, Zn, Al, Ce, La, Nd, Sc, Yb or In. Also, the metal catalyst is $RuCl_2$ and $CrCl_2$, and the $CrCl_2$ is from 300 to 500 parts by weight on the basis of 100 parts by weight of the $RuCl_2$.

When mixing metal catalyst and solvent to produce compound (S20), the solvent is desirable to be at least one of an ionic solvent or an aprotic polar solvent. Preferably, the ionic solvent is at least one of ethylmethylimidazolium chloride, ethylmethylimidazolium bromine or ethylmethylimidazolium iodine, etc, and the aprotic polar solvent is at least one of dimethylacetamide (DMA), dimethyl sulfoxide (DMSO), dimethylformamide (DMF), hexamethylphosphorous triamide, N-methylpyrrolidone, tetrahydrofuran or γ-butylorac.

The specific description about the above contents is the same with the description about the metal catalyst composition to produce furfural derivatives from lignocellulosic biomass raw materials.

Next, the heating (S21) is heating the compound. This is a mixing process to facilitate the reaction by mixing the solvent and the metal catalyst effectively.

When heating the compound (S21), temperature of heating is desirable to be from 60° C. to 100° C. and more preferably temperature of heating is effective to be from 80° C. to 90° C. For the temperature below 60° C., the metal catalyst is difficult to be dispersed effectively in solvent, and for the temperature above 100° C., there is a problem of economic value decreasing.

When heating the compound (S21), it is desirable to stir and heat at the same time. The time of heating and stirring is preferably is from 20 minute to 50 minute. More preferably, the time of 30 minute is effective. For the time below 20 minute, the metal catalyst is not dispersed enough, and for the time below 50 minute, there is a problem of economic value decreasing. Next, the adding (S22) is adding the lignocellulosic biomass material to the compound to produce reaction materials. This is a reaction preparing process to produce final product for the reaction by inputting biomass raw material.

When adding the lignocellulosic biomass material to the compound to produce reaction materials (S22), any lignocellulosic biomass is appropriate for the lignocellulosic biomass material. However, for the best effectiveness, the lignocellulosic biomass material is desirable to comprise at least one of cellulose or hemicellulose.

The cellulose which is a main component of lignocellulosic biomass used in the present invention is a linear natural polymer comprising D-glucose as a monomer. A hemicellulose is a natural polymer comprising D-xylose as a main monomer. Also, as shown in the chemical formula 2, a cellulose forms glycosidic bond in the position of C1 and C4 of D-glucose and is linked through β(1→4) bond. The bond of hemicellulose is formed in the position of C1 and C4 of D-xylose. A hemicellulose has two-dimensional chemical structure with some bonding lines unlike a linear polymer cellulose.

[Chemical Formula 2]

Cellulose

Hemicellulose

Also, in terms of chemical composition, lignocellulosic biomass is most effective to comprise at least one of 20% to 70% carbohydrate polymers (i.e. cellulose or hemicellulose).

Moreover, when adding the lignocellulosic biomass material to the compound to produce reaction materials (S22), the reaction material is desirable to be from 1 mole % to 20 mole % on the basis of 100 mole % of the lignocellulosic biomass raw material. More preferably, the reaction material mole from 5% to 10% is effective. The description about it is same with the ones in this specification.

Also, the lignocellulosic biomass material is desirable to be from 50 g to 500 g on the basis of the solvent 1 L. More preferably, the lignocellulosic biomass material from 100 g to 300 g is effective. When the lignocellulosic biomass material is below 50 g and above 500 g, there is a problem of a rapid decrease in yield, and the content rate of the described range in the present invention could maximize the yield.

The temperature of the adding (S22) is desirable to decrease in the heating (S21) and maintains from 15° C. to 30° C. More preferably, the temperature of the adding (S22) is effective to maintain from 20° C. to 25° C. For the temperature below 15° C., there is a problem of the compound and lignocellulosic raw material being damaged due to the low temperature. For the temperature above 30° C., some reactions could happen by adding lignocellulosic biomass raw material, which leads to a decrease in quality of the produced furfural derivatives and the yield.

Finally, a reacting (S23) is heating and reacting the reaction materials. This is a furfural derivatives producing process through conversion reaction.

When heating and reacting the reaction materials (S23), the temperature of reacting is desirable to be from 100° C. to 200° C. More preferably, the temperature of reacting is effective from 120° C. to 150° C. For the temperature below 100° C. there is a problem of enough reactions not happening. For the temperature above 200° C., a great amount of energy is consumed and the velocity of reacting increases sharply, which leads to a decrease in quality of the product, furfural derivatives and the yield.

When heating and reacting the reaction materials (S23), the time of reacting is desirable to be from 1 hour to 4 hours, and more preferably the time of reacting is effective to be from 2 hours to 3 hours. For the time of reacting below 1 hour, enough conversion reaction does not happen, and for the time of reacting above 4 hours economic values decrease, and quality of product decreases because additional reaction of the product and by-product happens.

Also, when heating and reacting the reaction materials (S23), it is desirable to stir and react reaction material by using a stirrer with a velocity from 500 RPM to 1000 RPM. The stirring could make all materials be reacted evenly, and as a result increase the reactivity and the yield.

Also, the velocity of the stirrer, from 500 RPM to 1000 RPM, could maximize the reactivity and the yield.

The conversion reaction of the present invention comprises a dissolve processing (a) for extracting polysaccharides, carbohydrate polymers from biomass supply source; a hydrolysis processing (b) for obtaining monosaccharide glucose or xylose from polysaccharide cellulose or hemicelluloses, a isomerization processing (c) for converting hexose glucose to pentagon glucose and a dehydration processing (d) for obtaining furan structure, and the all processes could be materialized at the same time in one reacting apparatus. Herein, in the conversion reaction, the various kinds of metal catalyst serves as a lewis acid to accelerate hydrolysis and dehydration reactions and mediate isomerization reaction which converts hexose structure to pentose structure.

The reaction formula 2 briefly shows the process of one example obtaining 5-hydroxymethyl-2-furfural and 2-furfural at the same time through single-step reaction from lignocellulosic biomass supply source which comprise carbohydrate polymer cellulose and hemicellulose as main components.

[Reaction Formula 2]

The starting material is a lignocellulosic biomass which comprises carbohydrate polymers cellulose and hemicelluloses as main components. Preferably, the lignocellulosic biomass could be obtained from plants that grow naturally with great vitality on non-cultivated lands (grass, reed, etc), crop residue after cultivation (rice straw, barley straw, wheat straw, corn stem, rape stem, etc), waste lignocellulosic resources (waste wood, waste paper, coffee residues, etc), etc.

Experiment results for proving the excellence of a composition of metal catalysts for preparation of furfural derivatives directly from lignocellulosic biomass raw materials and method of preparing furfural derivatives directly from lignocellulosic biomass raw materials using thereof will be examined.

The experiment results about the first example of producing furfural derivatives of the present invention are described below.

Producing Method

Metal catalysts (10 mol % of the substrate), 500 mg of solvent ionic liquid [EMIM]Cl were put into 6 mL of vial, the mixture was heated at 60° C. and stirred for 40 minutes. The mixture was cooled to room temperature and 50 mg of cellulose was poured into the mixture. And then the mixture was re-heated again at 90° C. to 120° C. and stirred at 700 rpm for 2 to 4 hours. After reactions were closed, the each vial was cooled to room temperature, diluted with 5 ml of HPLC grade distilled water and stirred for 40 minutes. After the each vial was diluted 100 fold, the each yield rate was measured through HPLC analysis. The each sample was separated through C18 reverse phase column on the HPLC (Varian Pro Star 310), and the peak area was measured by using UV detector (280 nm) and the yield rate was calculated back by using response factors obtained in advance.

Experiment 1: The Effect of Temperature on Reaction

The present reaction has a possibility of improving the yield rate under the condition of removing water with easiness through dehydration reaction. Therefore, each reaction of water at 90° C. which is lower than the boiling point and water at 120° C. which is higher than the boiling point was implemented and the effect of each temperature on reaction was observed. The time of reacting was 2 hours and the result is shown in the Table 1. As a result, the yield rate was better when the temperature on reaction was at 120° C. which is higher than the boiling point of water. The best yield rate, 19.1%, was obtained, when Cr (II) metal catalyst was used and the temperature of reacting was 120° C.

TABLE 1

The Effect of Reacting Temperature about Yield

| Order | Metal Catalyst | Solvent | Temperature (° C.) | Hours (h) | Yield (%) |
|---|---|---|---|---|---|
| 1 | CrCl$_2$ | [EMIM]Cl | 90 | 2 | 7.4 |
| 2 | CrCl$_2$ | [EMIM]Cl | 120 | 2 | 19.1 |
| 3 | MnCl$_2$ | [EMIM]Cl | 90 | 2 | 6.6 |
| 4 | MnCl$_2$ | [EMIM]Cl | 120 | 2 | 9.1 |
| 5 | FeCl$_2$ | [EMIM]Cl | 90 | 2 | 9.0 |
| 6 | FeCl$_2$ | [EMIM]Cl | 120 | 2 | 12.6 |
| 7 | FeCl$_3$ | [EMIM]Cl | 90 | 2 | 12.8 |
| 8 | FeCl$_3$ | [EMIM]Cl | 120 | 2 | 10.8 |
| 9 | CoCl$_2$6H$_2$O | [EMIM]Cl | 90 | 2 | 5.8 |
| 10 | CoCl$_2$6H$_2$O | [EMIM]Cl | 120 | 2 | 9.8 |
| 11 | NiCl$_2$ | [EMIM]Cl | 90 | 2 | 5.4 |
| 12 | NiCl$_2$ | [EMIM]Cl | 120 | 2 | 6.5 |
| 13 | CuCl$_2$ | [EMIM]Cl | 90 | 2 | 13.1 |
| 14 | CuCl$_2$ | [EMIM]Cl | 120 | 2 | 12.8 |
| 15 | ZnCl$_2$ | [EMIM]Cl | 90 | 2 | 6.7 |
| 16 | ZnCl$_2$ | [EMIM]Cl | 120 | 2 | 14.8 |

Experiment 2: The Effect of Reacting Time

The temperature of reaction was fixed at 120° C., the time of reacting was extended to 4 hours and the yield rate of HMF was measured. The yield rate increased from 19.1% to 27.1% when the chrome was used as catalyst, however, it is confirmed that when the rest of metal catalysts were used, the yield rate remained at the same or rather decreased. The reason seems to be the result of the creation of levulinic acid produced by additional dehydration reaction of the created HMF. The effect of reaction time on the yield rate of HMF is shown in the Table 2.

TABLE 2

The Effect of Reacting Time about HMF Yield

| Order | Metal Catalyst | Solvent | Temperature (° C.) | Hours (h) | Yield (%) |
|---|---|---|---|---|---|
| 1 | $CrCl_2$ | [EMIM]Cl | 120 | 2 | 19.1 |
| 2 | $CrCl_2$ | [EMIM]Cl | 120 | 4 | 27.1 |
| 3 | $MnCl_2$ | [EMIM]Cl | 120 | 2 | 9.1 |
| 4 | $MnCl_2$ | [EMIM]Cl | 120 | 4 | 10.9 |
| 5 | $FeCl_2$ | [EMIM]Cl | 120 | 2 | 12.6 |
| 6 | $FeCl_2$ | [EMIM]Cl | 120 | 4 | 9.2 |
| 7 | $FeCl_3$ | [EMIM]Cl | 120 | 2 | 10.8 |
| 8 | $FeCl_3$ | [EMIM]Cl | 120 | 4 | 6.8 |
| 9 | $CoCl_2 6H_2O$ | [EMIM]Cl | 120 | 2 | 9.8 |
| 10 | $CoCl_2 6H_2O$ | [EMIM]Cl | 120 | 4 | 9.6 |
| 11 | $NiCl_2$ | [EMIM]Cl | 120 | 2 | 6.5 |
| 12 | $NiCl_2$ | [EMIM]Cl | 120 | 4 | 6.1 |
| 13 | $CuCl_2$ | [EMIM]Cl | 120 | 2 | 12.8 |
| 14 | $CuCl_2$ | [EMIM]Cl | 120 | 4 | 9.5 |
| 15 | $ZnCl_2$ | [EMIM]Cl | 120 | 2 | 14.8 |
| 16 | $ZnCl_2$ | [EMIM]Cl | 120 | 4 | 6.0 |

Experiment 3: The Dual Catalyst System

From the result of above experiment, temperature of reaction was fixed at 120° C., the two metal catalysts were used simultaneously to convert the glucose into HMF. The time of reacting was 2 hours. Intriguingly, the yield rate on reaction increased significantly when the two catalysts were used simultaneously compared to that of the yield rate on reaction when only one catalyst was used. In particular, using combined metal catalysts including Cr (II) and Ru (III) made it possible to obtain about 60% of HMF. However, as it is confirmed in the result, the yield rate rather decreased when the time of reacting increased to 4 hours. The result is shown in the Table 3

TABLE 3

Dual Catalyst System

| Order | Metal catalyst 1 | Metal catalyst 2 | Solvent | Temperature (° C.) | Hours (h) | Yield (%) |
|---|---|---|---|---|---|---|
| 1 | $CrCl_2$ | $FeCl_2$ | [EMIM]Cl | 120 | 2 | 48.0 |
| 2 | $CrCl_2$ | $FeCl_2$ | [EMIM]Cl | 120 | 4 | 40.2 |
| 3 | $CrCl_2$ | $FeCl_3$ | [EMIM]Cl | 120 | 2 | 43.3 |
| 4 | $CrCl_2$ | $FeCl_3$ | [EMIM]Cl | 120 | 4 | 32.0 |
| 5 | $CrCl_2$ | $CuCl_2$ | [EMIM]Cl | 120 | 2 | 37.1 |
| 6 | $CrCl_2$ | $CuCl_2$ | [EMIM]Cl | 120 | 4 | 39.8 |
| 7 | $CrCl_2$ | $RuCl_3$ | [EMIM]Cl | 120 | 2 | 59.1 |
| 8 | $CrCl_2$ | $RuCl_3$ | [EMIM]Cl | 120 | 4 | 35.0 |

Experiment 4: The Effect of Catalyst Composition Rate in the Dual Catalyst System In order to optimize the composition rate of Cr(II) and Ru (III) which showed the best result in the dual catalyst system, the yield rate of HMF was measured by differentiating the composition rate. As a result, the best yield rate was obtained when the composition rate of Cr (II) and Ru (III) was 4:1. The result of each composition rate is shown in the Table 4.

TABLE 4

The Effect of Catalyst Composition Rate in Dual Catalyst System

| Order | Metal catalyst 1 | Metal catalyst 2 | Composition rate | Solvent | Temperature (° C.) | Hours (h) | Yield (%) |
|---|---|---|---|---|---|---|---|
| 1 | $CrCl_2$ | $RuCl_3$ | 10:1 | [EMIM]Cl | 120 | 2 | 37.6 |
| 2 | $CrCl_2$ | $RuCl_3$ | 6:1 | [EMIM]Cl | 120 | 2 | 51.3 |
| 3 | $CrCl_2$ | $RuCl_3$ | 5:1 | [EMIM]Cl | 120 | 2 | 53.1 |
| 4 | $CrCl_2$ | $RuCl_3$ | 4:1 | [EMIM]Cl | 120 | 2 | 59.6 |
| 5 | $CrCl_2$ | $RuCl_3$ | 3:1 | [EMIM]Cl | 120 | 2 | 54.6 |
| 6 | $CrCl_2$ | $RuCl_3$ | 2:1 | [EMIM]Cl | 120 | 2 | 53.6 |
| 7 | $CrCl_2$ | $RuCl_3$ | 1:1 | [EMIM]Cl | 120 | 2 | 54.2 |
| 8 | $CrCl_2$ | $RuCl_3$ | 1:2 | [EMIM]Cl | 120 | 2 | 34.1 |
| 9 | $CrCl_2$ | $RuCl_3$ | 1:3 | [EMIM]Cl | 120 | 2 | 31.2 |
| 10 | $CrCl_2$ | $RuCl_3$ | 1:4 | [EMIM]Cl | 120 | 2 | 28.5 |

Experiment 5: 3-Catalyst System

An experiment on 3-catalyst system was performed. Based on the result of the above experiment, manganese, copper and zinc metal catalysts were applied to dual catalysts of chrome and ruthenium, chrome and iron and chrome and copper. The temperature of reacting was fixed at 120° C. and the time of reacting was two hours. The best yield rate of HMF was obtained when the chrome, iron and manganese was used, however the result was not as good as that of the dual catalyst system. The result of 3-catalyst system is shown in the Table 5.

TABLE 5

Catalyst System

| Order | Metal catalyst 1 | Metal catalyst 2 | Metal catalyst 3 | Solvent | Temperature (° C.) | Hour(h) | Yield (%) |
|---|---|---|---|---|---|---|---|
| 1 | $CrCl_2$ | $FeCl_2$ | $MnCl_2$ | [EMIM]Cl | 120 | 2 | 38.0 |
| 2 | $CrCl_2$ | $FeCl_2$ | $CuCl_2$ | [EMIM]Cl | 120 | 2 | 31.1 |
| 3 | $CrCl_2$ | $FeCl_2$ | $ZnCl_2$ | [EMIM]Cl | 120 | 2 | 37.3 |
| 4 | $CrCl_2$ | $CuCl_2$ | $MnCl_2$ | [EMIM]Cl | 120 | 2 | 31.5 |
| 5 | $CrCl_2$ | $CuCl_2$ | $ZnCl_2$ | [EMIM]Cl | 120 | 2 | 29.4 |
| 6 | $CrCl_2$ | $RuCl_3$ | $FeCl_2$ | [EMIM]Cl | 120 | 2 | 32.7 |
| 7 | $CrCl_2$ | $RuCl_3$ | $MnCl_2$ | [EMIM]Cl | 120 | 2 | 33.3 |
| 8 | $CrCl_2$ | $RuCl_3$ | $CuCl_2$ | [EMIM]Cl | 120 | 2 | 22.7 |
| 9 | $CrCl_2$ | $RuCl_3$ | $ZnCl_2$ | [EMIM]Cl | 120 | 2 | 32.8 |

In conclusion, it was proven that HMF could be produced directly by high yield from cellulose extracted through metal catalyst conversion reaction from lignocellulosic biomass. Next, experiment results about the second example of furfural derivatives producing methods of the present invention are shown as below.

The component analysis results of cellulose and hemicellulose contents on various kinds of lignocellulosic biomass source supplies are shown as below in the Table 6.

TABLE 6

| Lignocellulosic biomass supply source | Component | | | |
|---|---|---|---|---|
| | Cellulose | Hemicellulose | Lignin | Ash |
| rice straw | 35.0 | 25.0 | 12.0 | — |
| barley straw | 37.0 | 22.2 | — | — |
| wheat straw | 38.2 | 21.2 | 23.4 | — |
| triticale | 35.8 | 24.3 | 21.9 | 7.4 |
| rape stem | 31.2 | 17.2 | 20.5 | 6.5 |
| grass | 39.7 | 26.4 | 24.3 | 2.4 |

TABLE 6-continued

| Lignocellulosic biomass supply source | Cellulose | Hemi-cellulose | Lignin | Ash |
|---|---|---|---|---|
| reed | 40.0 | 22.0 | 26.1 | 5.2 |
| MDF board | 33.2 | 12.1 | 32.2 | 1.1 |
| waste paper | 63.9 | 10.4 | 1.5 | 11.5 |
| coffee bean residue | 5.9 | 37.4 | 41.6 | 0.4 |

Exemplary Embodiment

Metal catalyst RuCl₃ and CrCl₂ (equivalent ratio 1:4 and equivalent total sum: 10 mole % of substrate), and ionic liquid solvent [EMIM]Cl (500 mg) were put in a tubular type reactor. And then, the mixture was heated at 90° C. and stirred for 30 minutes. After lowering the temperature of the mixture to room temperature, each of the lignocellulosic biomass raw materials (50 mg for each) shown in Table 1 was put in the mixture, reheated at 120° C. and stirred at 700 rpm for 2 hours. After the reaction was completed, each reactor was cooled to room temperature, diluted with HPLC grade distilled water. And then a each yield rate was measured for each reactor through HPLC analysis.

Figure 3:
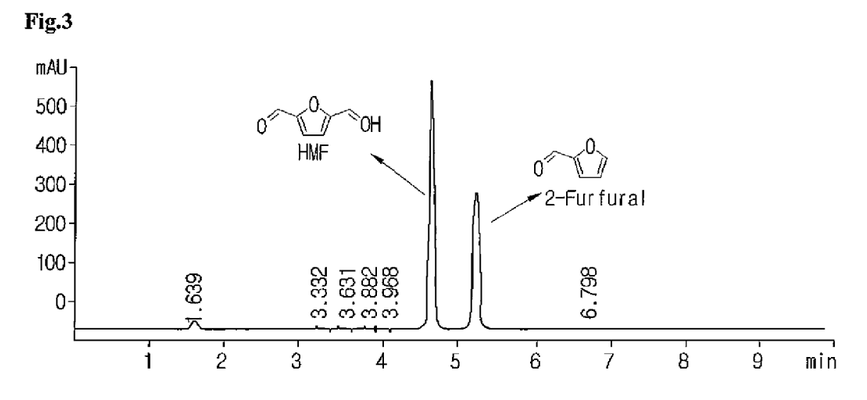
FIG. 3 is a graph of a high-performance liquid chromatography (HPLC) of product materials which are produced through the method for producing furfural derivatives of the present invention.
Figure 4:
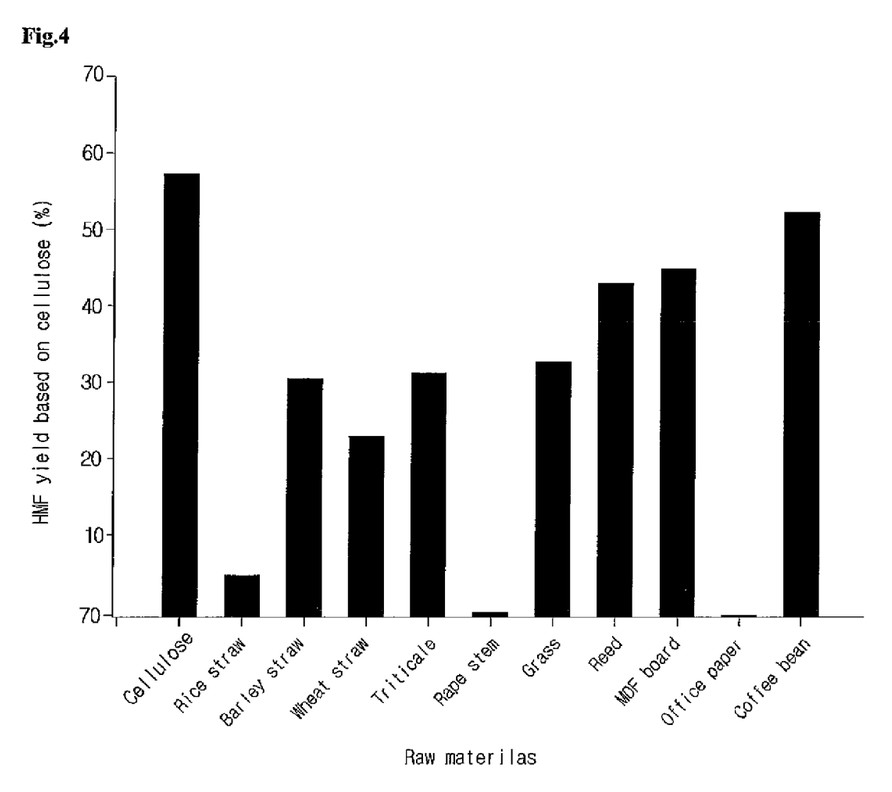
FIG. 4 is a graph for comparing each yield of 5-hydroxymethyl-2-furfurals product materials which are produced through the method for producing the furfural derivatives of the present invention according to lignocellulosic biomass raw materials.
Figure 5:
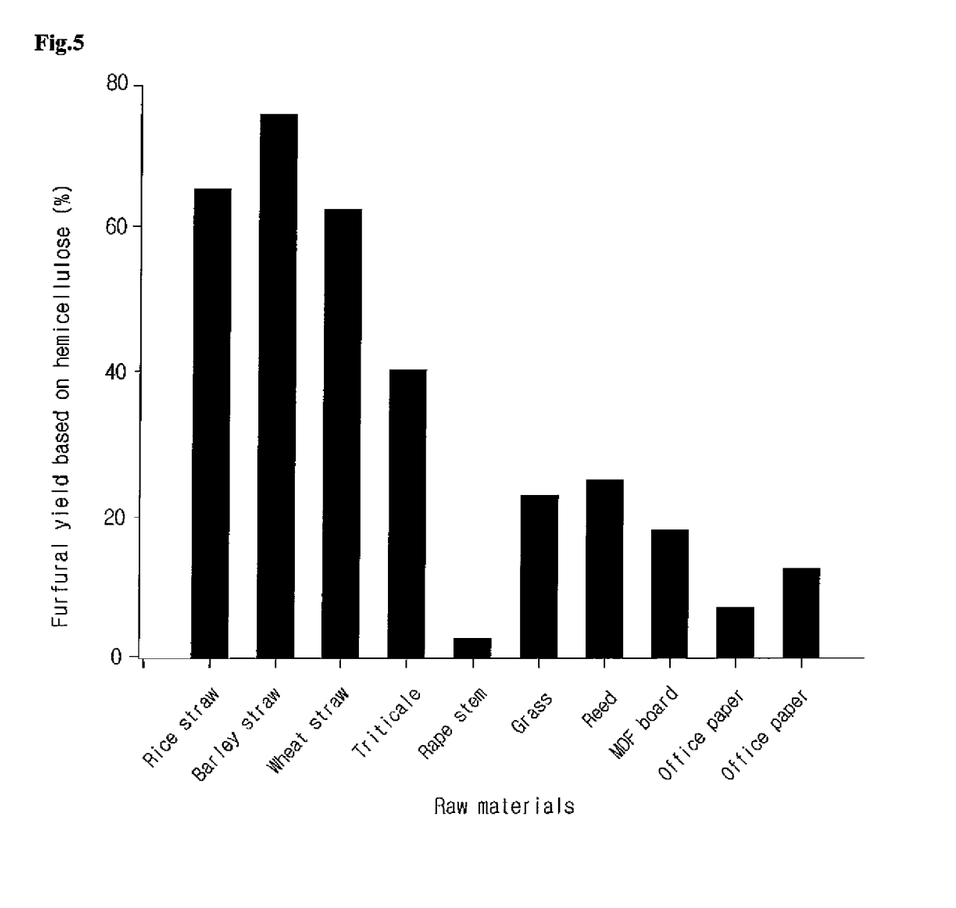
FIG. 5 is a graph for comparing each yield of 2-furfurals product materials which are produced through the method for producing the furfural derivatives of the present invention according to lignocellulosic biomass raw materials.

The sample was separated through C18 reverse phase column on high-performance liquid chromatography (HPLC; Agilent 1200 series), its peak area was measured through a UV detector (280 nm), and its yield was calculated back through a pre-obtained HMF response factor. Herein, the HPLC was as shown in FIG. 3, and each peak was confirmed as HMF and 2-furfural. According to the HPLC analysis results, the yield rate of the HMF and 2-furfural produced from each of the lignocellulosic biomass raw materials under the conversion reaction condition was as shown in FIG. 4 and FIG. 5.

Thus, the present experiment results in accordance with embodiments of the present invention show that each of the lignocellulosic biomass raw materials was converted into a furfural derivative effectively, and with an excellent yield rate.

INDUSTRIAL APPLICABILITY

The present invention relates to a metal catalyst composition for producing furfural derivatives from raw materials of lignocellulosic biomass, and method for producing furfural derivatives using the composition. More particularly to the composition and the method which may turn lignocellulosic biomass raw materials to furfural derivatives through single step process without additional saccharification process by using various kinds of metal catalyst in optimal reacting condition, thus significantly reducing process costs, unlike conventional composition and method going through multi step process.

What is claimed is:
1. A composition of metal catalysts and an ionic solvent for preparation of furfural derivatives from lignocellulosic biomass raw materials comprising a ruthenium and a chrome, wherein the chrome is from 300 to 500 parts by weight on the basis of 100 parts by weight of the ruthenium, and wherein the furfural derivative is either hydroxymethyl-2-furfural (HMF) having a structural formula of or 2-furfural having a structural formula of

2. The composition of metal catalysts for preparation of furfural derivatives from lignocellulosic biomass raw materials according to claim 1,
wherein the ionic solvent is at least one of ethylmethylimidazolium chloride, ethylmethylimidazolium bromine or ethylmethylimidazolium iodine.

3. A method for producing furfural derivatives comprising; extracting cellulose from lignocellulosic biomass; and reacting (1) metal catalyst of MXn or MXn.H₂O (M is a metal element, X is selected from the functional group consisting of halogen element, triflate, nonaflate, mesylate, tosylate or diazonium, and n is from 1 to 3) in an ionic solvent through catalyst conversion reaction to produce furfural derivatives, wherein the metal catalyst comprises Cr(II) metal catalyst and Ru(III) metal catalyst, and wherein the furfural derivative is either hydroxymethyl-2-furfural (HMF) having a structural formula of or 2-furfural having a structural formula of

4. The method for producing furfural derivatives according to claim 3;
wherein equivalence ratio of Cr(II) metal catalyst and Ru(III) metal catalyst is from 1:1 to 5:1.

5. The method for producing furfural derivatives according to claim 3;
wherein the ratio of a cellulose to ionic solvent is from 50 g/L to 500 g/L.

6. The method for producing furfural derivatives according to claim 3;
wherein temperature of reacting is from 100° C. to 150° C. and time of reacting is from 1 hour to 5 hours.

7. A method for producing furfural derivatives comprising:
mixing a metal catalyst and an ionic solvent to produce a compound;
heating the compound;
adding lignocellulosic biomass to the compound to produce reaction materials; and
reacting the reaction material by heating, wherein the metal catalyst comprises a ruthenium and a chrome when mixing the metal catalyst and the ionic solvent to produce the compound, wherein the chrome is from 300 parts to 500 parts by weight on the basis of 100 parts by weight of the ruthenium the furfural derivative is either hydroxymethyl-2-furfural (HMF) having a structural formula of or 2-furfural having a structural formula of 8. The method for producing furfural derivatives according to claim 7;
wherein the ionic solvent is at least one of ethylmethylimidazolium chloride, ethylmethylimidazolium bromine or ethylmethylimidazolium iodine.

9. The method for producing furfural derivatives according to claim 7;
wherein the temperature of heating is from 60° C. to 100° C.

10. The method for producing furfural derivatives according to claim 7;
wherein the lignocellulosic biomass raw material comprises at least one of a cellulose or a hemicellulose.

11. The method for producing furfural derivatives according to claim 7;
wherein the reaction material is from 1 mole % to 20 mole % on the basis of 100 mole % of the lignocellulosic biomass raw material.

12. The method for producing furfural derivatives according to claim 7;
wherein the lignocellulosic biomass raw material is from 50 g to 500 g on the basis of 1 L solvent.

13. The method for producing furfural derivatives according to claim 7;
wherein temperature of reacting is from 100° C. to 200° C., and time of reacting is from 1 hour to 4 hours.

* * * * *